United States Patent
Li et al.

(10) Patent No.: US 11,072,589 B2
(45) Date of Patent: Jul. 27, 2021

(54) 1,2,4-TRIAZOLE AND PREPARATION METHOD THEREFOR

(71) Applicant: SOOCHOW UNIVERSITY, Suzhou (CN)

(72) Inventors: Haiyan Li, Suzhou (CN); Huihuang Li, Suzhou (CN); Yaxiong Wang, Suzhou (CN); Xiaobing Wan, Suzhou (CN)

(73) Assignee: SOOCHOW UNIVERSITY

( * ) Notice: Subject to any disclaimer, the term of this patent is extended or adjusted under 35 U.S.C. 154(b) by 0 days.

(21) Appl. No.: 17/067,721

(22) Filed: Oct. 11, 2020

(65) Prior Publication Data

US 2021/0024472 A1    Jan. 28, 2021

Related U.S. Application Data

(63) Continuation of application No. PCT/CN2018/083136, filed on Apr. 15, 2018.

(51) Int. Cl.
*C07D 249/10*    (2006.01)
*B01J 23/72*    (2006.01)

(52) U.S. Cl.
CPC ............ *C07D 249/10* (2013.01); *B01J 23/72* (2013.01)

(58) Field of Classification Search
CPC .................................................. C07D 249/10
See application file for complete search history.

(56) References Cited

FOREIGN PATENT DOCUMENTS

| CN | 102388044 A | 3/2012 |
|---|---|---|
| CN | 108276350 A | 7/2018 |
| CN | 108373453 A | 8/2018 |
| WO | 2011060207 A1 | 5/2011 |

OTHER PUBLICATIONS

American Chemical Society STNext Registry, CAS RN: 2120488-67-5.

*Primary Examiner* — Patricia L Morris
(74) *Attorney, Agent, or Firm* — SZDC Law P.C.

(57) ABSTRACT

A method for preparing 1,2,4-triazole includes using a fluoroborate aryl diazonium salt, a diazoester derivative and an organic nitrile as reaction substrates, a transition metal salt as a catalyst, and an inorganic base as an additive in a cyclization reaction. The method has the following characteristics: the reaction is economical; the substrate is universal; the post-functionalization is easy; the reaction conditions are mild; the reaction can be performed in air; the catalyst amount used is less; and the post-treatment is simple. Meanwhile, the raw materials, such as the reactants and the catalyst used, are inexpensive and easily available; the reaction composition is reasonable; no ligand is needed; there are less reaction steps; and only one step of reaction is required to obtain a high yield, meeting the requirements and directions of contemporary green chemistry and medicinal chemistry, being suitable for screening highly active 1,2,4-triazole drugs.

7 Claims, No Drawings

1,2,4-TRIAZOLE AND PREPARATION METHOD THEREFOR

This application is a Continuation Application of PCT/CN2018/083136, filed on Apr. 15, 2018, which is incorporated by reference for all purposes as if fully set forth herein.

TECHNICAL FIELD

The invention relates to a method of preparing 1,2,4-triazole, and belongs to the technical field of organic synthesis.

BACKGROUND TECHNIQUE

As a valuable framework of five membered nitrogen-containing heterocycles, 1,2,4-triazole is widely used in many functional molecules and is used in the fields of organic catalysis and materials science. In addition, the 1,2,4-triazole skeleton is also found in many bioactive molecules and has important applications in the pharmaceutical industry and pesticides. At present, the preparation of 1,2,4-triazole has many disadvantages such as many reaction steps, complicated preparation of raw materials, complicated reaction conditions, and narrow substrate range. For example:

(1) Michael J. Stocks et al. reported the preparation of 1,2,4-triazole from primary amines, amide diacetal derivatives, and hydrazide derivatives, but requires multiple steps and a narrow reaction substrate (see: Michael J. Stocks; Org Lett. 2004, 6, 2969);

(2) Hideko Nagasawa et al. reported the preparation of 1,2,4-triazole by hydrazine hydrochloride derivatives and organic nitriles, but the reaction temperature is high and the substrate range is narrow (see: Hideko Nagasawa; J. Am. Chem. Soc. 2009, 131, 15080);

(3) Recently, Bo Tang et al. reported the preparation of 1,2,4-triazole with a nitrogen heterocyclopropene derivative, azodicarboxylate and bromide as the reaction substrate, but the reaction was carried out in two steps, and the raw materials were Multi-step synthesis is required (see: Bo Tang; Chem. Commun. 2017, 53, 9644).

Therefore, it is necessary to develop a preparation method with abundant raw materials, high reactivity, low cost, and simple operation to efficiently synthesize 1,2,4-triazole compounds.

SUMMARY OF INVENTION

Technical Problem

The object of the present invention is to provide a method preparation of 1,2,4-triazole, which has a rich source of reaction materials, a wide universality of the reaction substrate, simple operation and convenient synthesis of potential drug molecules in the later stage.

Technical Solution

In order to achieve the above object, the technical solution adopted by the present invention is:

In one embodiment, a method of preparing a 1,2,4-triazole includes: conducting a cyclization reaction of a fluoroborate aryl diazonium salt, a diazonium ester derivative and an organic nitrile, in the presence of a copper salt as a catalyst and an inorganic base as an additive, to obtain the 1,2,4-triazole. The fluoroborate aryl diazonium salt has the following chemical structural formula:

and Ar is selected from the group consisting of an aryl group, a monosubstituted aryl group, a disubstituted aryl group, and naphthyl; the diazonium ester derivative has the following chemical formula:

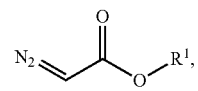

and $R^1$ is selected from the group consisting of ethyl, isopropyl, tert-butyl, cyclohexyl, phenyl, benzyl,

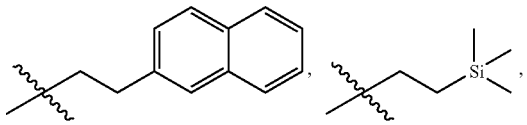

—$CH_2CH_2CH_2OCH_3$, —$CH_2CF_3$, —$CH_2CH_2Br$,

and —$CH_2CH_2CH$=$CH_2$; the organic nitrile has the following chemical structural formula: $R^2$—C≡N, and $R^2$ is selected form the group consisting of methyl, isopropyl, tert-butyl, benzyl, —$CH_2CH_2CH_2Cl$, —$CH_2CH_2OCH_3$, —$CH_2CH$=$CH_2$, —$CH$=$CHCH_3$, and

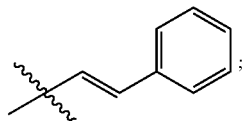 [SMILES: */C=C/c1ccccc1]

the 1,2,4-triazole has the following chemical structural formula:

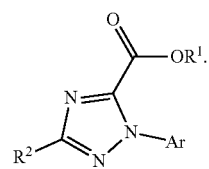

In another embodiment, the cyclization reaction is conducted at 40° C. for 1 hour in the air.

In another embodiment, the copper salt was a halogen copper salt, and the additive is selected from the group consisting of lithium carbonate, potassium carbonate, cesium carbonate, sodium acetate, and lithium tert-butoxide.

In another embodiment, the copper salt is cuprous bromide, and the additive is lithium carbonate.

In another embodiment, the aryl group is phenyl; the monosubstituted aryl group has the following chemical structural formula:

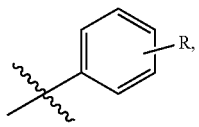

and R is selected from the group consisting of hydrogen, methyl, isopropyl, tert-butyl, isopropyl, methoxy, fluoride, chlorine, bromine, trifluoromethyl, and trifluoromethoxy; and the disubstituted aryl group is selected from the group consisting of

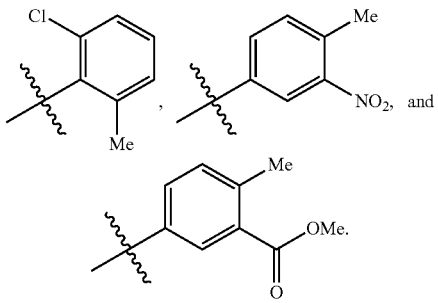

In another embodiment, a molar ratio of the catalyst to the fluoroborate aryl diazonium salt is 20%; and a molar ratio of the additive to the fluoroborate aryl diazonium salt is 1.

In another embodiment, a molar ratio of the organic nitrile to the fluoroborate aryl diazonium salt is 20-50; and a molar ratio of the diazonium ester derivative to the fluoroborate aryl diazonium salt is 3.

The cyclization reaction of the present invention is carried out in the air, and after completion of the reaction, it is quenched with ethyl acetate, then the solvent is removed by a rotary evaporator, and the silica gel is adsorbed. Finally, a simple column chromatography is carried out using a mixed solvent of ethyl acetate and petroleum ether. The product 1,2,4-triazole can be obtained. Therefore, the present invention also discloses 1,2,4-triazole prepared according to the above method.

Advantageous Effects of the Invention

Beneficial Effect

Due to the use of the above technical solutions, the present invention has the following advantages over the prior art:

1. In the present invention, copper bromide is preferably used as a catalyst, and lithium carbonate is used as an additive to realize cyclization reaction of aryl fluoroborate of fluoroborate, diazo ester derivative and organic nitrile to prepare 1,2,4-triazole, and present In the technical pre-preparation of raw materials, many reaction steps and harsh conditions, the reaction is more economical, the substrate is more universal, and the raw materials are easy to obtain. It is easier to functionalize later.

2. The method disclosed in the invention has mild reaction conditions, can be carried out in air, has a small amount of catalyst, and is easy to be post-treated, which is beneficial to purification of products and large-scale industrial application, and one-step functionalization of commercial drugs is easier to carry out.

3 The reactants, catalysts and the like used in the invention are cheap and easy to obtain, have a reasonable reaction composition, do not require a ligand, have few reaction steps, and can obtain a high yield in a single reaction, which meets the requirements of contemporary green chemistry and medicinal chemistry. Direction, suitable for screening highly active 1,2,4-triazole drugs. Invention embodiment

EMBODIMENTS OF THE INVENTION

The present invention is further described below in conjunction with the embodiments:

The raw materials, catalysts and additives of the invention are all market-oriented commodities, and can be directly purchased or prepared according to conventional techniques. For example, the aryl diazonium fluoroborate can be obtained by reacting a marketed aromatic amine, sodium nitrite and fluoroboric acid; The diazo ester derivative can be synthesized by a commercially available alcohol with a simple starting material such as bromoacetyl bromide, p-toluenesulfonyl hydrazide or p-toluenesulfonyl chloride.

Example 1

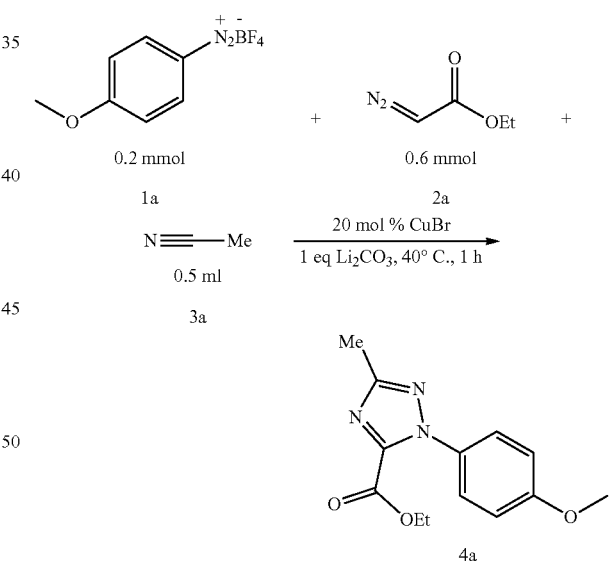

Compound 1a (0.2 mmol, 45.8 mg), CuBr (0.04 mmol, 5.8 mg), $Li_2CO_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4a was obtained by simple column chromatography with a yield of 85%. The main test data of the product are as follows. The analysis shows that the actual synthetic product is consistent with the theoretical analysis.

$^1$H NMR (400 MHz, CDCl$_3$) δ 7.33-7.25 (m, 4H), 4.36 (q, J=8.0 Hz, 2H), 2.51 (s, 3H), 2.43 (s, 3H), 1.34 (t, J=8.0 Hz, 3H). $^{13}$C NMR (101 MHz, CDCl$_3$) δ 160.79, 157.28, 144.66, 139.60, 135.29, 129.33, 125.31, 62.38, 21.15, 13.89, 13.72. HRMS (ESI-TOF): Anal. Calcd. For C$_{13}$H$_{15}$N$_3$O$_2$+ Na$^+$: 284.1006, Found: 284.1015; IR (neat, cm$^{-1}$): ν 2936.42, 1731.74, 1519.50, 1255.34, 1234.01, 1112.29, 1107.30, 827.78.

Example 2

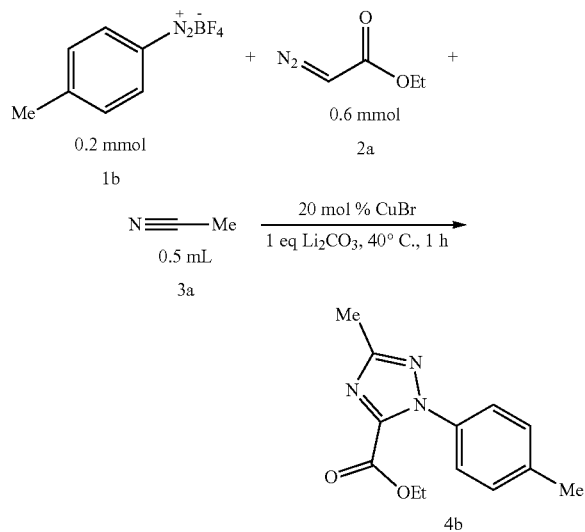

Compound 1b (0.2 mmol, 43.4 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4b was obtained by simple column chromatography with a yield of 71%. The main test data of the product are as follows. The analysis shows that the actual synthetic product is consistent with the theoretical analysis.

$^1$H NMR (400 MHz, CDCl$_3$) δ 7.33-7.25 (m, 4H), 4.36 (q, J=8.0 Hz, 2H), 2.51 (s, 3H), 2.43 (s, 3H), 1.34 (t, J=8.0 Hz, 3H). $^{13}$C NMR (101 MHz, CDCl$_3$) δ 160.79, 157.28, 144.66, 139.60, 135.29, 129.33, 125.31, 62.38, 21.15, 13.89, 13.72. HRMS (ESI-TOF): Anal. Calcd. For C$_{13}$H$_{15}$N$_3$O$_2$+ H$^+$: 246.1237, Found: 246.1235; IR (neat, cm$^{-1}$): ν 2986.72, 1728.32, 1518.54, 1300.80, 1229.34, 1118.00, 1052.76, 816.07.

Example 3

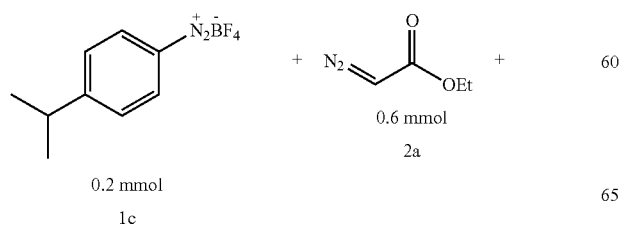

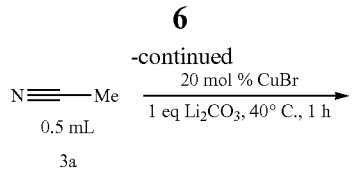

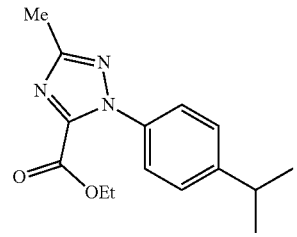

Compound 1c (0.2 mmol, 49.3 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4c was obtained by simple column chromatography with a yield of 70%. The main test data of the product are as follows. The analysis shows that the actual synthetic product is consistent with the theoretical analysis.

$^1$H NMR (400 MHz, CDCl$_3$) δ 7.38-7.30 (m, 4H), 4.36 (q, J=8.0 Hz, 2H), 2.99 (dt, J=13.8, 6.9 Hz, 1H), 2.51 (s, 3H), 1.33 (t, J=8.0 Hz, 3H), 1.28 (d, J=6.9 Hz, 6H). $^{13}$C NMR (101 MHz, CDCl$_3$) δ 160.80, 157.31, 150.40, 144.63, 135.51, 126.77, 125.38, 62.38, 33.82, 23.76, 13.87, 13.72. HRMS (ESI-TOF): Anal. Calcd. For C$_{15}$H$_{19}$N$_3$O$_2$+H$^+$: 274.1550, Found: 274.1549; IR (neat, cm$^{-1}$): ν 2960.85, 1739.54, 1521.23, 1224.84, 1115.14, 1057.49, 853.78, 837.46.

Example 4

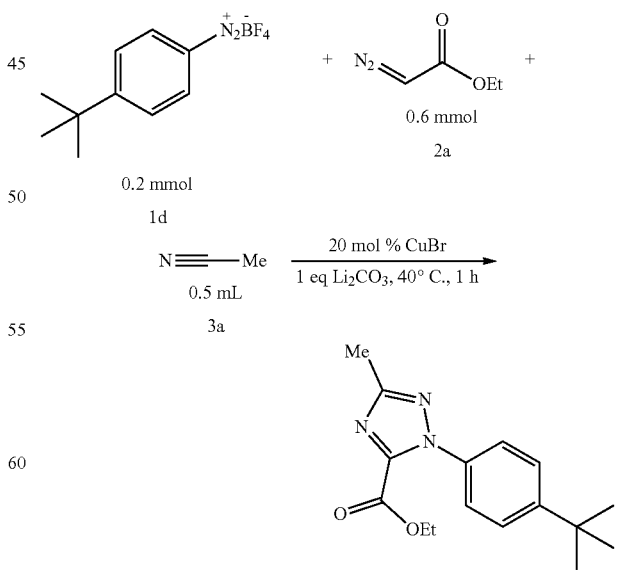

Compound 1d (0.2 mmol, 52.3 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4d was obtained by simple column chromatography with a yield of 66%. The main test data of the product are as follows. The analysis shows that the actual synthetic product is consistent with the theoretical analysis.

$^1$H NMR (400 MHz, CDCl$_3$) δ 7.52-7.46 (m, 2H), 7.39-7.32 (m, 2H), 4.37 (q, J=8.0 Hz, 2H), 2.51 (s, 3H), 1.38-1.30 (m, 12H). $^{13}$C NMR (101 MHz, CDCl$_3$) δ 160.79, 157.32, 152.65, 144.60, 135.21, 125.70, 125.02, 62.37, 34.73, 31.16, 13.88, 13.73. HRMS (ESI-TOF): Anal. Calcd. For C$_{16}$H$_{21}$N$_3$O$_2$+Na$^+$: 310.1526, Found: 310.1536; IR (neat, cm$^{-1}$): ν 2962.52, 1740.86, 1523.31, 1483.23, 1227.50, 1104.75, 1055.22, 841.35.

Example 5

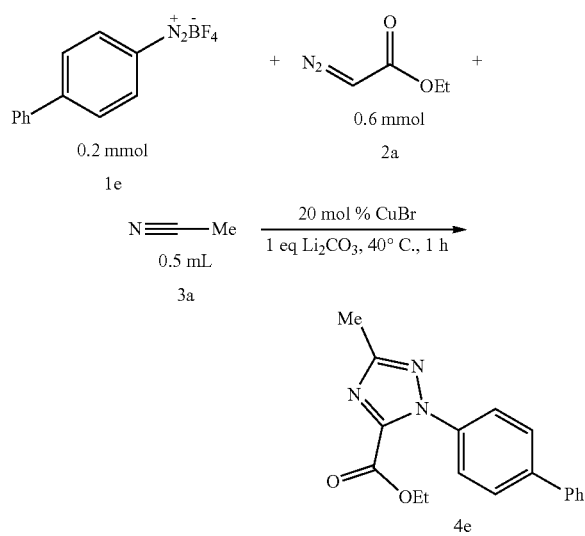

Compound 1e (0.2 mmol, 56.5 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4e was obtained by simple column chromatography with a yield of 52%. The main test data of the product are as follows. The analysis shows that the actual synthetic product is consistent with the theoretical analysis.

$^1$H NMR (400 MHz, CDCl$_3$) δ 7.74-7.67 (m, 2H), 7.62 (m, 2H), 7.54-7.44 (m, 4H), 7.42-7.36 (m, 1H), 4.39 (q, J=8.0 Hz, 2H), 2.53 (s, 3H), 1.36 (t, J=7.1 Hz, 3H). $^{13}$C NMR (101 MHz, CDCl$_3$) δ 161.07, 157.37, 144.74, 142.48, 139.74, 136.86, 128.85, 127.86, 127.46, 127.16, 125.88, 62.56, 13.97, 13.80. HRMS (ESI-TOF): Anal. Calcd. For C$_{18}$H$_{17}$N$_3$O$_2$+Na$^+$: 330.1213, Found: 330.1220; IR (neat, cm$^{-1}$): ν 2920.13, 1745.02, 1299.15, 1220.32, 1112.49, 1055.96, 770.05, 705.14.

Example 6

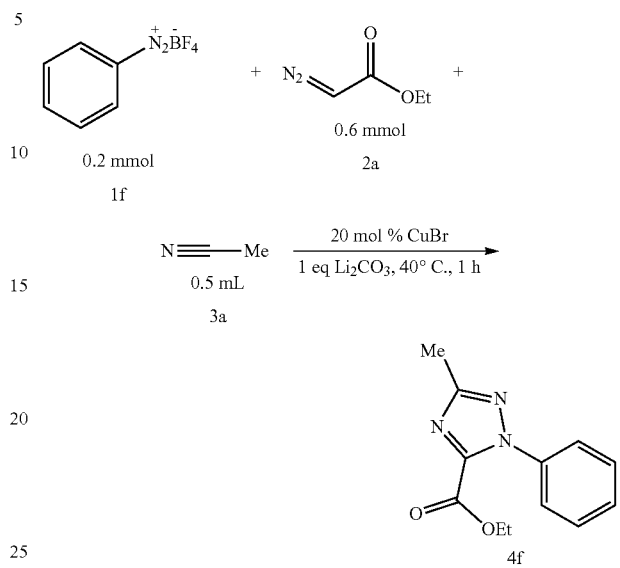

Compound 1f (0.2 mmol, 40.4 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4f was obtained by simple column chromatography with a yield of 64%. The main test data of the product are as follows. The analysis shows that the actual synthetic product is consistent with the theoretical analysis.

$^1$H NMR (400 MHz, CDCl$_3$) δ 7.51-7.46 (m, 3H), 7.46-7.41 (m, 2H), 4.36 (q, J=8.0 Hz, 2H), 2.52 (s, 3H), 1.32 (t, J=8.0 Hz, 3H). $^{13}$C NMR (101 MHz, CDCl$_3$) δ 160.86, 157.15, 144.66, 137.72, 129.38, 128.70, 125.50, 62.36, 13.80, 13.65. HRMS (ESI-TOF): Anal. Calcd. For C$_{12}$H$_{13}$N$_3$O$_2$+Na$^+$: 254.0900, Found: 254.0903; IR (neat, cm$^{-1}$): ν 2986.08, 1734.75, 1509.89, 1227.99, 1118.24, 1053.52, 765.16, 694.81.

Example 7

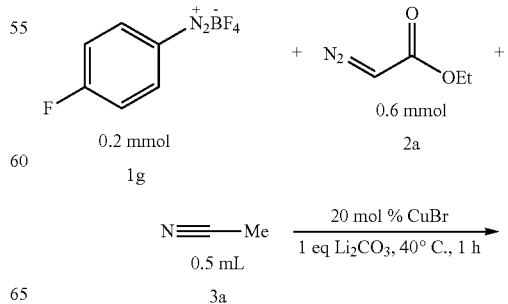

-continued

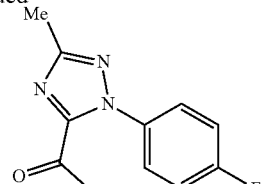

4g

Compound 1g (0.2 mmol, 44.2 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4g was obtained by simple column chromatography with a yield of 60%. The main test data of the product are as follows. The analysis shows that the actual synthetic product is consistent with the theoretical analysis.

$^1$H NMR (400 MHz, CDCl$_3$) δ 7.53-7.32 (m, 2H), 7.23-7.06 (m, 2H), 4.37 (q, J=8.0 Hz, 2H), 2.51 (s, 3H), 1.35 (t, J=8.0 Hz, 3H). $^{13}$C NMR (101 MHz, CDCl$_3$) δ 164.00, 161.51, 160.99, 157.10, 144.75, 133.82, 133.79, 127.64, 127.55, 115.87, 115.64, 62.52, 13.87, 13.67. HRMS (ESI-TOF): Anal. Calcd. For C$_{12}$H$_{12}$FN$_3$O$_2$+Na$^+$: 272.0806, Found: 272.0801; IR (neat, cm$^{-1}$): ν 2987.77, 1728.00, 1517.03, 1484.20, 1232.15, 1122.99, 1051.12, 834.38.

Example 8

Compound 1h (0.2 mmol, 47.7 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4h was obtained by simple column chromatography with a yield of 54%. The main test data of the product are as follows. The analysis shows that the actual synthetic product is consistent with the theoretical analysis.

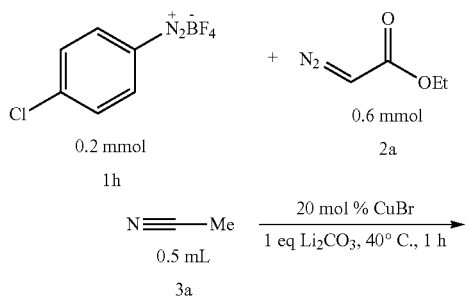

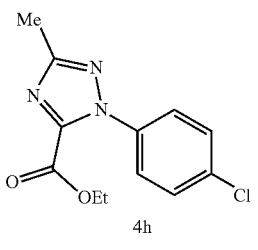

4h $^1$H NMR (400 MHz, CDCl$_3$) δ 7.52-7.43 (m, 2H), 7.42-7.34 (m, 2H), 4.38 (q, J=8.0 Hz, 2H), 2.51 (s, 3H), 1.36 (t, J=8.0 Hz, 3H). $^{13}$C NMR (101 MHz, CDCl$_3$) δ 161.23, 157.20, 144.76, 136.24, 135.48, 129.01, 126.96, 62.66, 13.95, 13.75. HRMS (ESI-TOF): Anal. Calcd. For C$_{12}$H$_{12}$ClN$_3$O$_2$+Na$^+$: 288.0510, Found: 288.0499; IR (neat, cm$^{-1}$): ν 2923.78, 1728.88, 1479.44, 1302.47, 1235.60, 1100.73, 1051.74, 830.37.

Example 9

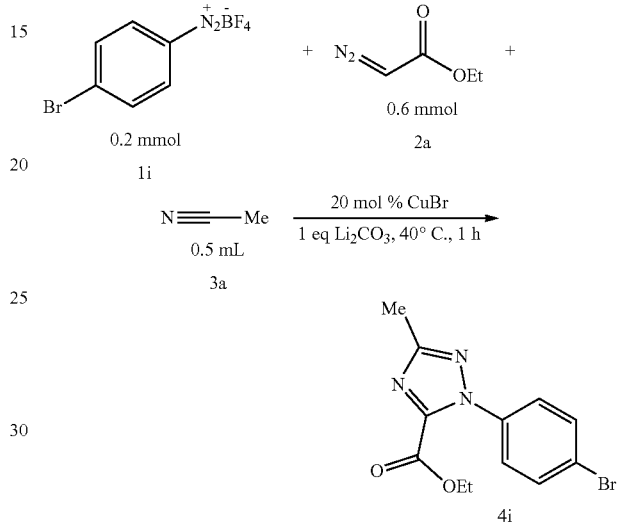

Compound 1i (0.2 mmol, 56.0 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4i was obtained by simple column chromatography with a yield of 53%. The main test data of the product are as follows. The analysis shows that the actual synthetic product is consistent with the theoretical analysis.

$^1$H NMR (400 MHz, CDCl$_3$) δ 7.79-7.51 (m, 2H), 7.40-7.24 (m, 2H), 4.38 (q, J=8.0 Hz, 2H), 2.51 (s, 3H), 1.36 (t, J=8.0 Hz, 3H). $^{13}$C NMR (101 MHz, CDCl$_3$) δ 161.3, 157.2, 144.7, 136.7, 132.0, 127.2, 123.5, 62.7, 14.0, 13.8. HRMS (ESI-TOF): Anal. Calcd. For C$_{12}$H$_{12}$BrN$_3$O$_2$+Na$^+$: 332.0005, 333.9985, Found: 332.0006, 333.9983; IR (neat, cm$^{-1}$): ν 2977.70, 1728.33, 1497.41, 1301.34, 1235.41, 1122.10, 1099.21, 827.50.

Example 10

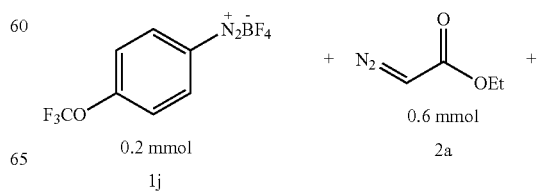

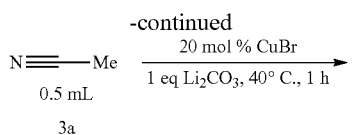

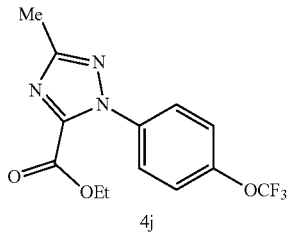

Compound 1j (0.2 mmol, 58.1 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4j was obtained by simple column chromatography with a yield of 46%. The main test data of the product are as follows. The analysis shows that the actual synthetic product is consistent with the theoretical analysis.

$^1$H NMR (400 MHz, CDCl$_3$) δ 7.58-7.45 (m, 2H), 7.34 (d, J=8.4 Hz, 2H), 4.38 (q, J=8.0 Hz, 2H), 2.52 (s, 3H), 1.35 (t, J=8.0 Hz, 3H). $^{13}$C NMR (101 MHz, CDCl$_3$) δ 161.31, 157.18, 149.58, 144.83, 136.13, 127.35, 121.15, 62.71, 13.92, 13.76. HRMS (ESI-TOF): Anal. Calcd. For C$_{13}$H$_{12}$F$_3$N$_3$O$_3$+Na$^+$: 338.0723, Found: 338.0718; IR (neat, cm$^{-1}$): ν 2990.01, 1741.28, 1517.71, 1257.97, 1203.59, 1161.03, 1122.05, 860.53.

Example 11

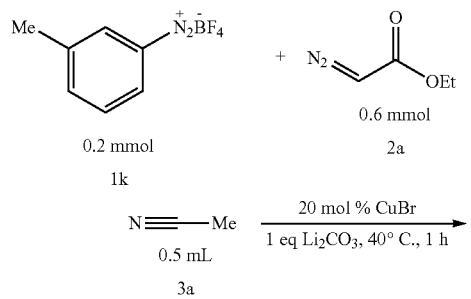

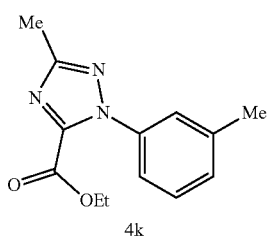

Compound 1k (0.2 mmol, 43.4 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4k was obtained by simple column chromatography with a yield of 69%. The main test data of the product are as follows. The analysis shows that the actual synthetic product is consistent with the theoretical analysis.

$^1$H NMR (400 MHz, CDCl$_3$) δ 7.36 (m, 1H), 7.29 (m, 1H), 7.27-7.19 (m, 1H), 4.36 (q, J=8.0 Hz, 2H), 2.51 (s, 3H), 2.42 (s, 3H), 1.33 (t, J=8.0 Hz, 3H). $^{13}$C NMR (101 MHz, CDCl$_3$) δ 160.87, 157.27, 144.73, 139.01, 137.70, 130.24, 128.54, 126.04, 122.66, 62.41, 21.16, 13.89, 13.73. HRMS (ESI-TOF): Anal. Calcd. For C$_{13}$H$_{15}$N$_3$O$_2$+Na$^+$: 268.1056, Found: 268.1060; IR (neat, cm$^{-1}$): ν 2925.21, 1732.17, 1504.01, 1231.72, 1115.47, 1062.54, 796.71, 694.59.

Example 12

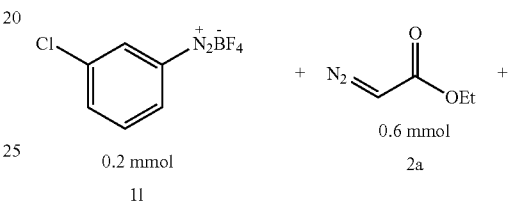

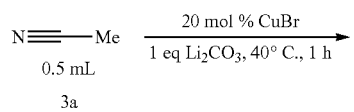

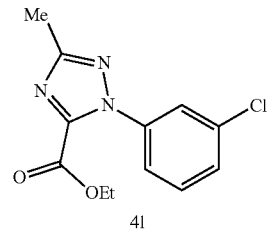

Compound 1l (0.2 mmol, 47.7 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4l was obtained by simple column chromatography with a yield of 46%. The main test data of the product are as follows. The analysis shows that the actual synthetic product is consistent with the theoretical analysis.

$^1$H NMR (400 MHz, CDCl$_3$) δ 7.67-7.59 (m, 2H), 7.43-7.33 (m, 2H), 4.38 (q, J=8.0 Hz, 2H), 2.51 (s, 3H), 1.35 (t, J=8.0 Hz, 3H). $^{13}$C NMR (101 MHz, CDCl$_3$) δ 161.30, 157.08, 144.83, 138.72, 132.58, 129.96, 128.85, 124.41, 122.10, 62.67, 13.91, 13.73. HRMS (ESI-TOF): Anal. Calcd. For C$_{12}$H$_{12}$ClN$_3$O$_2$+Na$^+$: 288.0510, Found: 288.0519; IR (neat, cm$^{-1}$): ν 2918.90, 1728.46, 1504.34, 1296.90, 1233.04, 1122.62, 786.51, 682.53.

Example 13

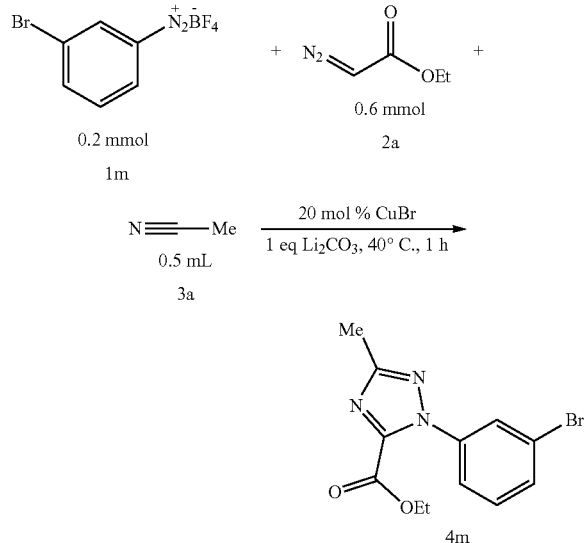

Compound 1m (0.2 mmol, 56.0 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4m was obtained by simple column chromatography with a yield of 40%. The main test data of the product are as follows. The analysis shows that the actual synthetic product is consistent with the theoretical analysis.

$^1$H NMR (400 MHz, CDCl$_3$) δ 7.50-7.46 (m, 2H), 7.45-7.40 (m, 1H), 7.37-7.33 (m, 1H), 4.38 (q, J=8.0 Hz, 2H), 2.51 (s, 3H), 1.35 (t, J=8.0 Hz, 3H). $^{13}$C NMR (101 MHz, CDCl$_3$) δ 161.28, 157.08, 144.82, 138.65, 134.50, 129.76, 129.72, 126.08, 123.97, 62.73, 13.93, 13.74. HRMS (ESI-TOF): Anal. Calcd. For C$_{12}$H$_{12}$BrN$_3$O$_2$+Na$^+$: 332.0005, 333.9985, Found: 332.0016, 333.9995; IR (neat, cm$^{-1}$): ν 2935.73, 1731.12, 1472.25, 1231.83, 1123.08, 867.37, 790.69, 682.99.

Example 14

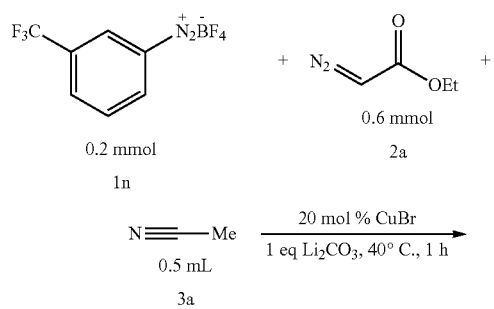

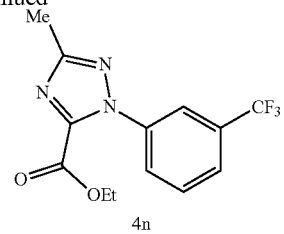

Compound 1n (0.2 mmol, 54.8 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4n was obtained by simple column chromatography with a yield of 31%. The main test data of the product are as follows. The analysis shows that the actual synthetic product is consistent with the theoretical analysis.

$^1$H NMR (400 MHz, CDCl$_3$) δ 7.80-7.73 (m, 2H), 7.69-7.60 (m, 2H), 4.38 (q, J=8.0 Hz, 2H), 2.53 (s, 3H), 1.34 (t, J=8.0 Hz, 3H). $^{13}$C NMR (101 MHz, CDCl$_3$) δ 161.48, 157.07, 144.88, 138.17, 131.96, 131.63, 131.30, 130.97, 129.41, 129.04, 126.23, 126.20, 126.16, 126.12, 124.59, 122.96, 122.92, 122.89, 122.85, 121.88, 62.73, 13.84, 13.70. HRMS (ESI-TOF): Anal. Calcd. For C$_{13}$H$_{12}$F$_3$N$_3$O$_2$+H$^+$: 300.0954, Found: 300.0955; IR (neat, cm$^{-1}$): ν 2957.27, 1735.31, 1329.97, 1282.83, 1187.40, 1167.55, 1121.79, 803.91.

Example 15

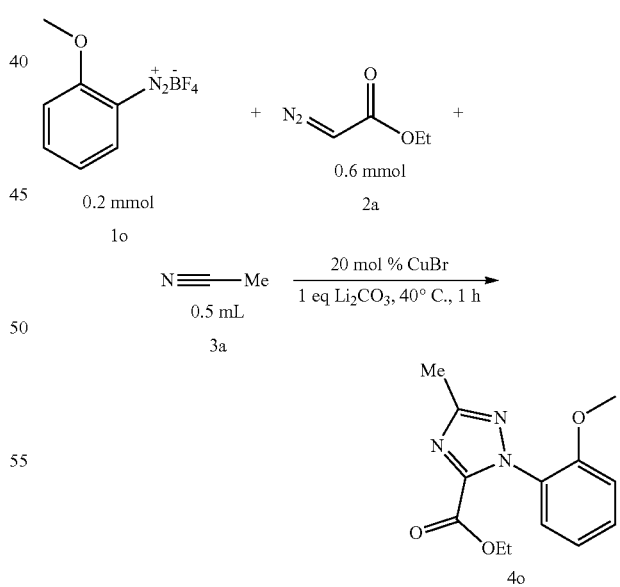

Compound to (0.2 mmol, 45.0 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4o was obtained by simple column chromatography with a yield of 62%. The main test data of the product are as follows. The analysis shows that the actual synthetic product is consistent with the theoretical analysis.

$^1$H NMR (400 MHz, CDCl$_3$) δ 7.48-7.41 (m, 1H), 7.39 (m, 1H), 7.07 (m, 1H), 7.01 (m, 1H), 4.32 (q, J=8.0 Hz, 2H), 3.75 (s, 3H), 2.51 (s, 3H), 1.29 (t, J=8.0 Hz, 3H). $^{13}$C NMR (101 MHz, CDCl$_3$) δ 160.87, 157.18, 153.34, 146.25, 130.74, 127.15, 126.88, 120.57, 111.54, 62.02, 55.53, 13.84, 13.77. HRMS (ESI-TOF): Anal. Calcd. For C$_{13}$H$_{15}$N$_3$O$_3$+Na$^+$: 284.1006, Found: 284.0993; IR (neat, cm$^{-1}$): ν 2919.79, 1731.90, 1494.78, 1290.07, 1248.55, 1100.45, 1038.55, 781.89.

Example 16

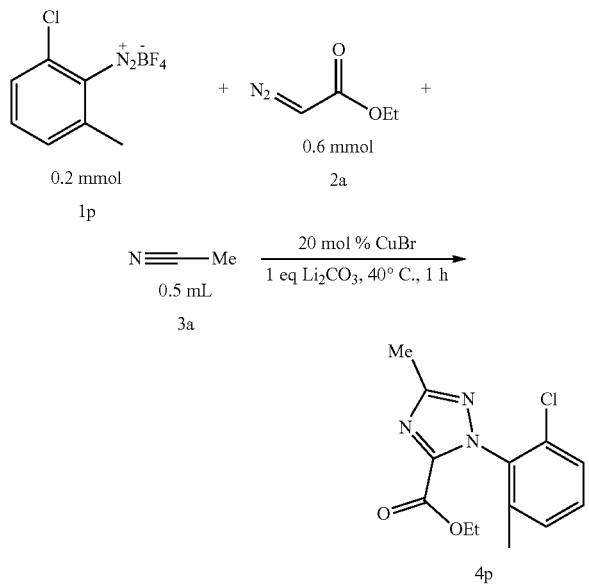

Compound 1p (0.2 mmol, 50.6 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4p was obtained by simple column chromatography with a yield of 63%. The main test data of the product are as follows. The analysis shows that the actual synthetic product is consistent with the theoretical analysis.

$^1$H NMR (400 MHz, CDCl$_3$) δ 7.39-7.30 (m, 2H), 7.28-7.23 (m, 1H), 4.33 (q, J=8.0 Hz, 2H), 2.56 (s, 3H), 2.08 (s, 3H), 1.28 (t, J=8.0 Hz, 3H). $^{13}$C NMR (101 MHz, CDCl$_3$) δ 161.96, 156.60, 146.00, 137.50, 135.30, 131.80, 130.53, 129.05, 127.32, 62.43, 17.68, 13.95, 13.82. HRMS (ESI-TOF): Anal. Calcd. For C$_{13}$H$_{14}$ClN$_3$O$_2$+Na$^+$: 302.0667, Found: 302.0677; IR (neat, cm$^{-1}$): ν 2969.18, 1729.02, 1448.87, 1231.15, 1119.39, 1086.66, 1039.00, 800.42.

Example 17

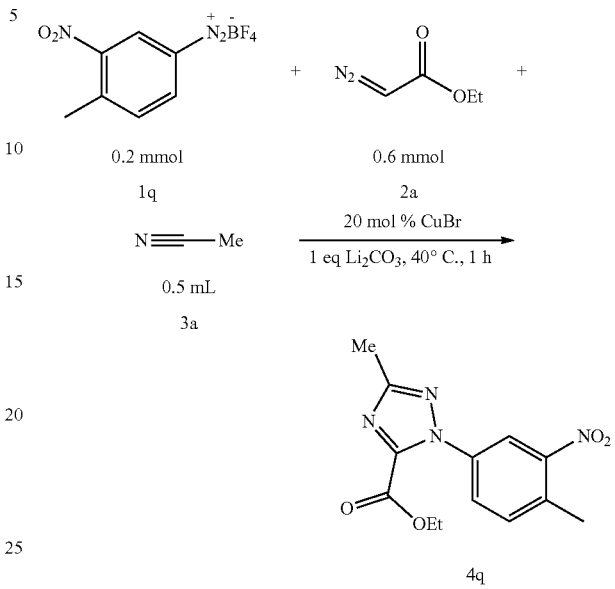

Compound 1q (0.2 mmol, 52.9 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4q was obtained by simple column chromatography with a yield of 41%. The main test data of the product are as follows. The analysis shows that the actual synthetic product is consistent with the theoretical analysis.

$^1$H NMR (400 MHz, CDCl$_3$) δ 8.15 (d, J=2.2 Hz, 1H), 7.64 (dd, J=8.2, 2.2 Hz, 1H), 7.49 (d, J=8.3 Hz, 1H), 4.41 (q, J=8.0 Hz, 2H), 2.70 (s, 3H), 2.52 (s, 3H), 1.38 (t, J=8.0 Hz, 3H). $^{13}$C NMR (101 MHz, CDCl$_3$) δ 161.58, 157.13, 148.59, 144.79, 136.25, 135.09, 133.11, 129.91, 122.26, 62.88, 20.41, 13.94, 13.73. HRMS (ESI-TOF): Anal. Calcd. For C$_{13}$H$_{14}$N$_4$O$_4$+Na$^+$: 313.0907, Found: 313.0915; IR (neat, cm$^{-1}$): ν 2922.97, 1726.18, 1532.44, 1483.18, 1349.06, 1295.79, 1123.24, 1079.32.

Example 18

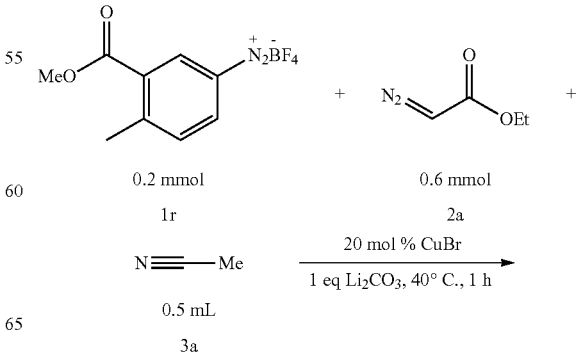

-continued

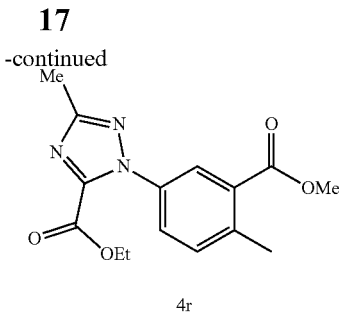

4r

Compound 1r (0.2 mmol, 55.6 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4r was obtained by simple column chromatography with a yield of 39%. The main test data of the product are as follows. The analysis shows that the actual synthetic product is consistent with the theoretical analysis.

$^1$H NMR (400 MHz, CDCl$_3$) δ 8.03 (d, J=2.3 Hz, 1H), 7.48 (dd, J=8.2, 2.4 Hz, 1H), 7.38 (d, J=8.2 Hz, 1H), 4.38 (q, J=8.0 Hz, 2H), 3.90 (s, 3H), 2.69 (s, 3H), 2.52 (s, 3H), 1.35 (t, J=8.0 Hz, 3H). $^{13}$C NMR (101 MHz, CDCl$_3$) δ 166.47, 161.15, 157.22, 144.77, 142.09, 135.57, 132.16, 129.86, 128.82, 127.87, 62.59, 52.04, 21.55, 13.93, 13.76. HRMS (ESI-TOF): Anal. Calcd. For C$_{15}$H$_{17}$N$_3$O$_4$+Na$^+$: 326.1111, Found: 326.1123; IR (neat, cm$^{-1}$): ν 2921.53, 1723.83, 1509.26, 1310.41, 1222.22, 1119.70, 1086.25, 781.90.

Example 19

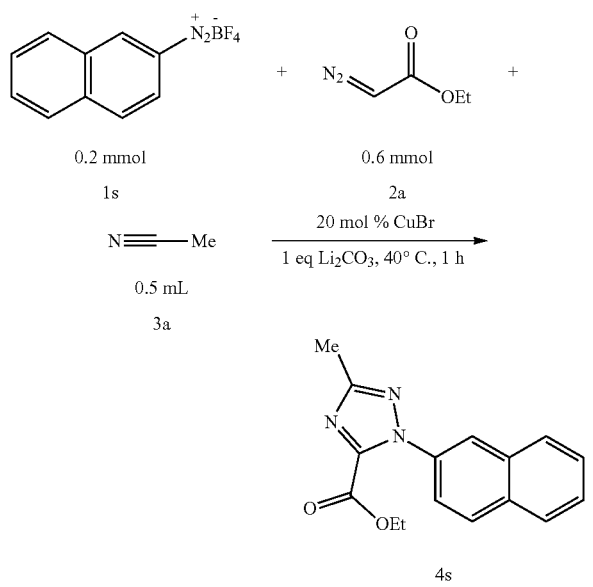

Compound 1s (0.2 mmol, 51.0 mg), CuBr (0.04 mmol, 5.8 mg), Li$_2$CO$_3$ (14.8 mmol), compound 3a (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 4s was obtained by simple column chromatography with a yield of 61%. The main test data of the product are as follows. The analysis shows that the actual synthetic product is consistent with the theoretical analysis.

$^1$H NMR (400 MHz, CDCl$_3$) δ 7.91 (m, 4H), 7.62-7.46 (m, 3H), 4.36 (q, J=8.0 Hz, 2H), 2.55 (s, 3H), 1.30 (t, J=8.0 Hz, 3H). $^{13}$C NMR (101 MHz, CDCl$_3$) δ 161.08, 157.33, 144.95, 135.14, 133.19, 132.66, 128.75, 128.28, 127.80, 127.23, 127.02, 124.43, 123.25, 62.51, 13.92, 13.81. HRMS (ESI-TOF): Anal. Calcd. For C$_{16}$H$_{15}$N$_3$O$_2$+Na$^+$: 304.1056, Found: 304.1066; IR (neat, cm$^{-1}$): ν 2935.17, 1727.51, 1302.74, 1246.98, 1109.87, 1057.21, 811.15, 745.81.

Example 20

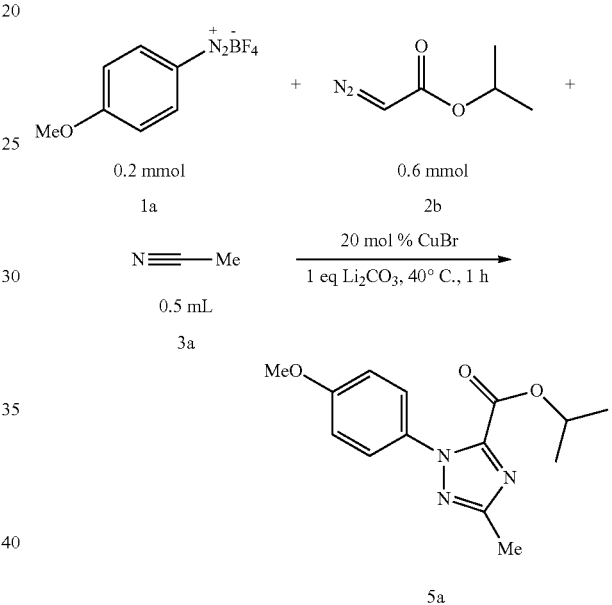

Compound 1a (0.2 mmol, 45.8 mg), CuBr (0.04 mmol, 5.8 mg), Li$_2$CO$_3$ (14.8 mmol), compound 3a (0.5 ml) and compound 2b (0.6 mmol, 78.5 mg) were successively loaded into the reaction flask. Then the system was stirred at 40° C. in air for 1 hour, then quenched with ethyl acetate, the solvent was removed by rotary evaporator, and silica gel adsorption was carried out. The product 5a was obtained by simple column chromatography with a yield of 85%. The main test data of the product are as follows. The analysis shows that the actual synthetic product is consistent with the theoretical analysis.

$^1$H NMR (400 MHz, CDCl$_3$) δ 7.38-7.30 (m, 2H), 7.03-6.93 (m, 2H), 5.19 (dt, J=12.6, 6.3 Hz, 1H), 3.85 (s, 3H), 2.50 (s, 3H), 1.30 (d, J=6.3 Hz, 6H). $^{13}$C NMR (101 MHz, CDCl$_3$) δ 160.60, 160.07, 156.83, 145.08, 130.82, 126.82, 113.76, 70.47, 55.38, 21.37, 13.69. HRMS (ESI-TOF): Anal. Calcd. For C$_{14}$H$_{17}$N$_3$O$_3$+H$^+$: 276.1343, Found: 276.1355; IR (neat, cm$^{-1}$): ν 2984.11, 1722.12, 1518.55, 1303.28, 1244.48, 1126.76, 1102.00, 827.13.

Example 21

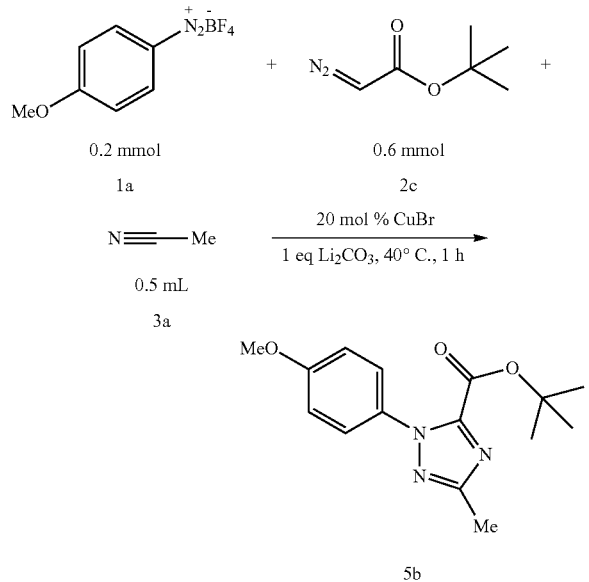

Compound 1a (0.2 mmol, 45.8 mg), CuBr (0.04 mmol, 5.8 mg), Li₂CO₃ (14.8 mmol), compound 3a (0.5 ml) and compound 2c (0.6 mmol, 87.1 mg) were successively loaded into the reaction flask. Then the system was stirred at 40° C. in air for 1 hour, then quenched with ethyl acetate, the solvent was removed by rotary evaporator, and silica gel adsorption was carried out. The product 5b was obtained by simple column chromatography with a yield of 46%. The main test data of the product are as follows. The analysis shows that the actual synthetic product is consistent with the theoretical analysis.

$^1$H NMR (400 MHz, CDCl$_3$) δ 7.34-7.29 (m, 2H), 7.01-6.93 (m, 2H), 3.86 (s, 3H), 2.49 (s, 3H), 1.47 (s, 9H). $^{13}$C NMR (101 MHz, CDCl$_3$) δ 160.53, 160.08, 156.43, 146.13, 131.16, 126.79, 113.90, 84.20, 55.49, 27.73, 13.78. HRMS (ESI-TOF): Anal. Calcd. For C$_{15}$H$_{19}$N$_3$O$_3$+H$^+$: 290.1499, Found: 290.1507; IR (neat, cm$^{-1}$): ν 2924.07, 1732.96, 1516.63, 1250.67, 1234.74, 1114.37, 1102.41, 836.77.

Example 22

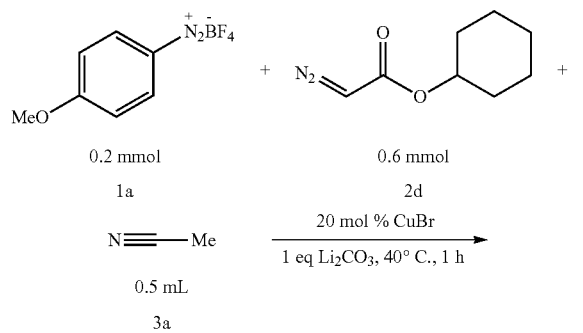

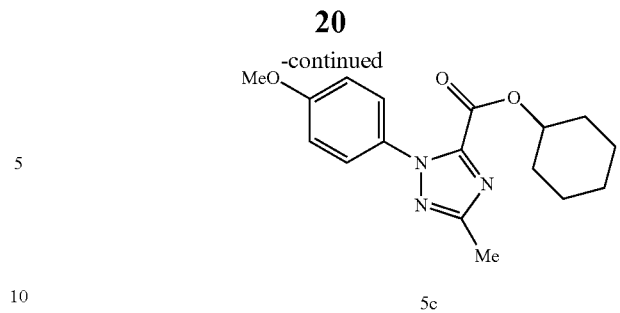

Compound 1a (0.2 mmol, 45.8 mg), CuBr (0.04 mmol, 5.8 mg), Li$_2$CO$_3$ (14.8 mmol), compound 3a (0.5 ml) and compound 2d (0.6 mmol, 103.0 mg) were successively loaded into the reaction flask. Then the system was stirred at 40° C. in air for 1 hour, then quenched with ethyl acetate, the solvent was removed by rotary evaporator, and silica gel adsorption was carried out. The product 5c was obtained by simple column chromatography with a yield of 70%. The main test data of the product are as follows. The analysis shows that the actual synthetic product is consistent with the theoretical analysis.

$^1$H NMR (400 MHz, CDCl$_3$) δ 7.38-7.29 (m, 2H), 7.03-6.89 (m, 2H), 5.02-4.86 (m, 1H), 3.86 (s, 3H), 2.56-2.46 (s, 3H), 1.94-1.85 (m, 2H), 1.73-1.62 (m, 2H), 1.58-1.40 (m, 3H), 1.37-1.15 (m, 3H). $^{13}$C NMR (101 MHz, CDCl$_3$) δ 160.68, 160.13, 156.86, 145.26, 130.94, 126.88, 113.85, 75.60, 55.47, 31.18, 24.97, 23.69, 13.76. HRMS (ESI-TOF): Anal. Calcd. For C$_{17}$H$_{21}$N$_3$O$_3$+Na$^+$: 338.1475, Found: 338.1463; IR (neat, cm$^{-1}$): ν 2936.47, 1731.18, 1518.58, 1251.82, 1221.23, 1117.26, 1049.51, 839.39.

Example 23

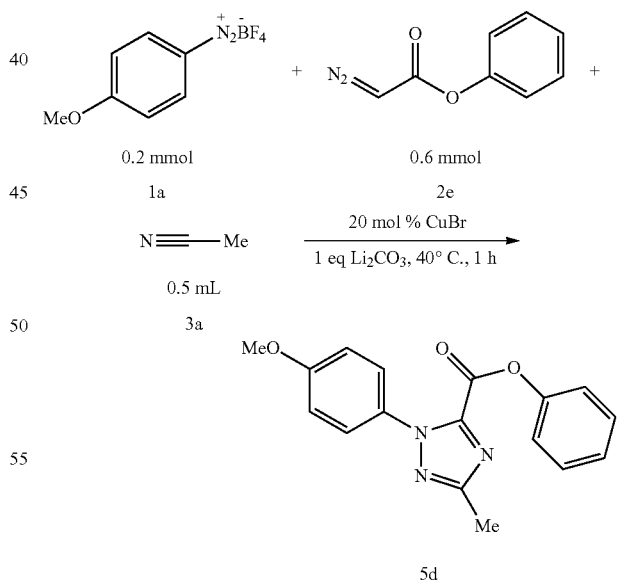

Compound 1a (0.2 mmol, 45.8 mg), CuBr (0.04 mmol, 5.8 mg), Li$_2$CO$_3$ (14.8 mmol) compound 3a (0.5 ml) and compound 2e (0.6 mmol, 99.3 mg) were successively loaded into the reaction flask. Then the system was stirred at 40° C. in air for 1 hour, then quenched with ethyl acetate, the solvent was removed by rotary evaporator, and silica gel adsorption was carried out. The product 5d was obtained by simple column chromatography with a yield of 86%. The main test data of the product are as follows. The analysis shows that the actual synthetic product is consistent with the theoretical analysis.

$^1$H NMR (400 MHz, CDCl$_3$) δ 7.43-7.33 (m, 4H), 7.27-7.21 (m, 1H), 7.18-7.12 (m, 2H), 6.99-6.93 (m, 2H), 3.81 (s, 3H), 2.58 (s, 3H). $^{13}$C NMR (101 MHz, CDCl$_3$) δ 161.08, 160.28, 155.79, 149.73, 144.06, 130.50, 129.42, 126.89, 126.42, 121.21, 113.96, 55.46, 13.80. HRMS (ESI-TOF): Anal. Calcd. For C$_{17}$H$_{15}$N$_3$O$_3$+H$^+$: 310.1186, Found: 310.1177; IR (neat, cm$^{-1}$): ν 2823.11, 1741.42, 1302.15, 1250.80, 1232.35, 830.89, 750.85, 725.17.

Example 24

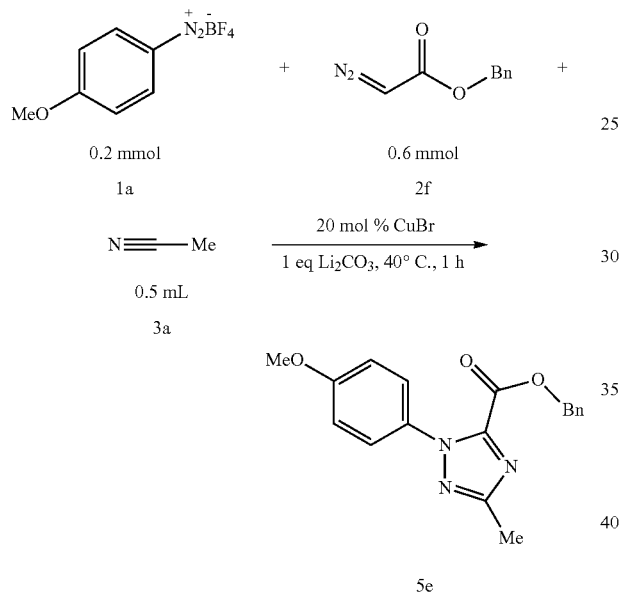

Example 25

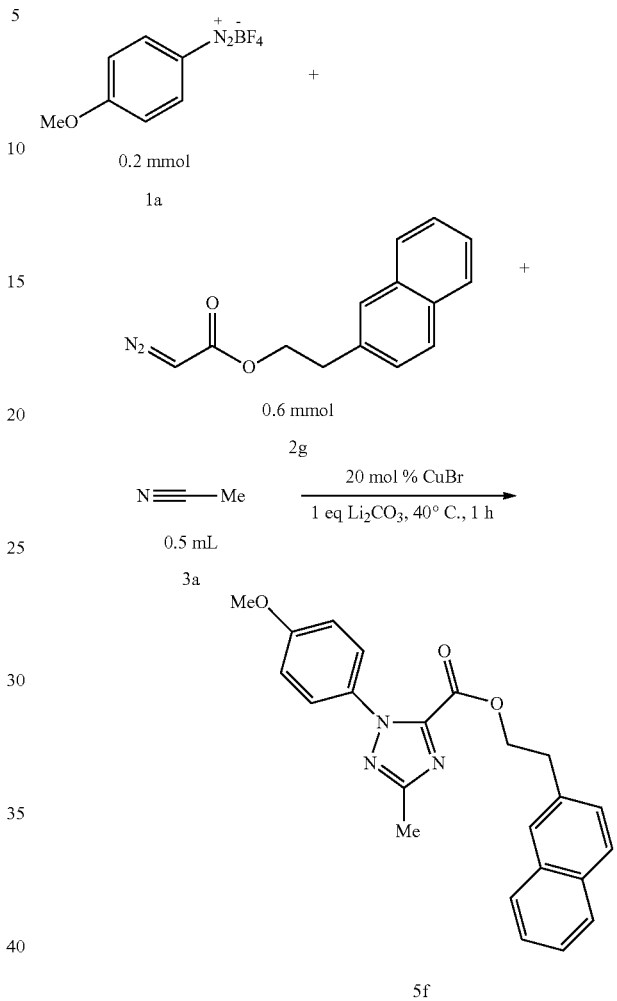

Compound 1a (0.2 mmol, 45.8 mg), CuBr (0.04 mmol, 5.8 mg), Li$_2$CO$_3$ (14.8 mmol), compound 3a (0.5 ml) and compound 2f (0.6 mmol, 107.9 mg) were successively loaded into the reaction flask. Then the system was stirred at 40° C. in air for 1 hour, then quenched with ethyl acetate, the solvent was removed by rotary evaporator, and silica gel adsorption was carried out. The product 5e was obtained by simple column chromatography with a yield of 72%. The main test data of the product are as follows. The analysis shows that the actual synthetic product is consistent with the theoretical analysis.

$^1$H NMR (400 MHz, CDCl$_3$) δ 7.43-7.16 (m, 7H), 6.99-6.78 (m, 2H), 5.30 (s, 2H), 3.83 (s, 3H), 2.49 (s, 3H). $^{13}$C NMR (101 MHz, CDCl$_3$) δ 160.81, 160.14, 157.10, 144.60, 134.39, 130.66, 128.66, 128.54, 128.45, 126.82, 113.88, 67.81, 55.41, 13.72. HRMS (ESI-TOF): Anal. Calcd. For C$_{18}$H$_{17}$N$_3$O$_3$+H$^+$: 324.1343, Found: 324.1350; IR (neat, cm$^{-1}$): ν 2992.11, 1728.03, 1517.60, 1300.65, 1251.15, 1239.09, 1120.72, 1105.86.

Compound 1a (0.2 mmol, 45.8 mg), CuBr (0.04 mmol, 5.8 mg), Li$_2$CO$_3$ (14.8 mmol), compound 3a (0.5 ml) and compound 2g (0.6 mmol, 147.2 mg) were successively loaded into the reaction flask. Then the system was stirred at 40° C. in air for 1 hour, then quenched with ethyl acetate, the solvent was removed by rotary evaporator, and silica gel adsorption was carried out. The product 5f was obtained by simple column chromatography with a yield of 84%. The main test data of the product are as follows. The analysis shows that the actual synthetic product is consistent with the theoretical analysis.

$^1$H NMR (400 MHz, CDCl$_3$) δ 8.03 (d, J=8.2 Hz, 1H), 7.87-7.82 (m, 1H), 7.74 (d, J=8.1 Hz, 1H), 7.53-7.44 (m, 2H), 7.40-7.34 (m, 1H), 7.30 (d, J=6.4 Hz, 1H), 7.28-7.23 (m, 2H), 6.95-6.87 (m, 2H), 4.68-4.58 (t, J=8.0 Hz, 2H), 3.80 (s, 3H), 3.48 (t, J=8.0 Hz, 2H), 2.52 (s, 3H). $^{13}$C NMR (101 MHz, CDCl$_3$) δ 160.78, 160.12, 157.19, 144.51, 133.73, 132.57, 131.80, 130.60, 128.72, 127.55, 126.97, 126.74, 126.24, 125.64, 125.41, 123.27, 113.84, 65.89, 55.40, 31.88, 13.74. HRMS (ESI-TOF): Anal. Calcd. For C$_{23}$H$_{21}$N$_3$O$_3$+H$^+$: 388.1656, Found: 388.1645; IR (neat, cm$^{-1}$): ν 2964.75, 1732.15, 1517.85, 1253.72, 1214.09, 1115.14, 840.27, 809.79.

Example 26

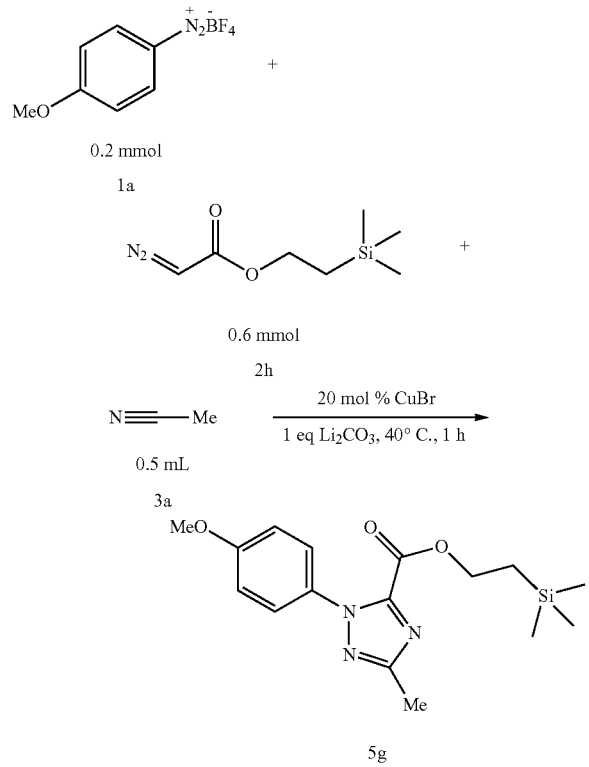

Compound 1a (0.2 mmol, 45.8 mg), CuBr (0.04 mmol, 5.8 mg), Li$_2$CO$_3$ (14.8 mmol), compound 3a (0.5 ml) and compound 2h (0.6 mmol, 114.1 mg) were successively loaded into the reaction flask. Then the system was stirred at 40° C. in air for 1 hour, then quenched with ethyl acetate, the solvent was removed by rotary evaporator, and silica gel adsorption was carried out. The product 5g was obtained by simple column chromatography with a yield of 53%. The main test data of the product are as follows. The analysis shows that the actual synthetic product is consistent with the theoretical analysis.

$^1$H NMR (400 MHz, CDCl$_3$) δ 7.48-7.29 (m, 2H), 7.08-6.89 (m, 2H), 4.47-4.30 (m, 2H), 3.86 (s, 3H), 2.50 (s, 3H), 1.19-0.95 (m, 2H), 0.03 (2, 9H). $^{13}$C NMR (101 MHz, CDCl$_3$) δ 160.71, 160.17, 157.49, 144.87, 130.76, 126.88, 113.89, 64.97, 55.46, 17.38, 13.76, −1.73. HRMS (ESI-TOF): Anal. Calcd. For C$_{16}$H$_{23}$N$_3$O$_3$Si+H$^+$: 334.1581, Found: 334.1585; IR (neat, cm$^{-1}$): ν 2954.63, 1737.78, 1517.88, 1250.59, 1230.20, 1118.37, 866.69, 829.30.

Example 27

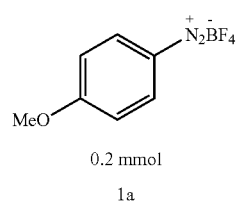

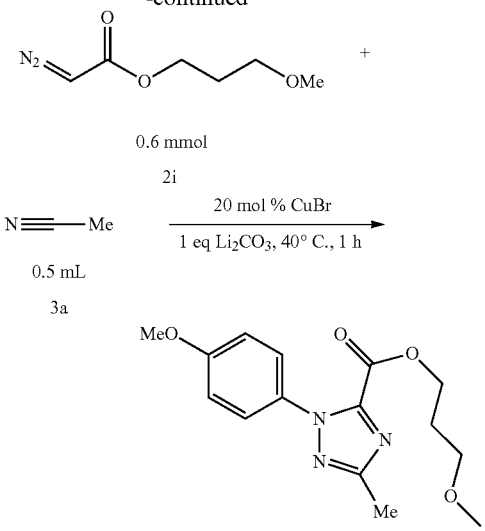

Compound 1a (0.2 mmol, 45.8 mg), CuBr (0.04 mmol, 5.8 mg), Li$_2$CO$_3$ (14.8 mmol), compound 3a (0.5 ml) and compound 2i (0.6 mmol, 96.9 mg) were successively loaded into the reaction flask. Then the system was stirred at 40° C. in air for 1 hour, then quenched with ethyl acetate, the solvent was removed by rotary evaporator, and silica gel adsorption was carried out. The product 5h was obtained by simple column chromatography with a yield of 85%. The main test data of the product are as follows. The analysis shows that the actual synthetic product is consistent with the theoretical analysis.

$^1$H NMR (400 MHz, CDCl$_3$) δ 7.38-7.31 (m, 2H), 7.02-6.94 (m, 2H), 4.38 (t, J=8.0 Hz, 2H), 3.86 (s, 3H), 3.37 (t, J=6.2 Hz, 2H), 3.29 (s, 3H), 2.50 (s, 3H), 1.99-1.91 (m, 2H). $^{13}$C NMR (101 MHz, CDCl$_3$) δ 160.79, 160.21, 157.31, 144.73, 130.78, 126.88, 113.92, 68.67, 63.68, 58.55, 55.48, 28.60, 13.75. HRMS (ESI-TOF): Anal. Calcd. For C$_{15}$H$_{19}$N$_3$O$_4$+Na$^+$: 328.1268, Found: 328.1266; IR (neat, cm$^{-1}$): ν 2926.65, 1736.51, 1518.71, 1252.57, 1217.87, 1116.87, 1050.56, 837.62.

Example 28

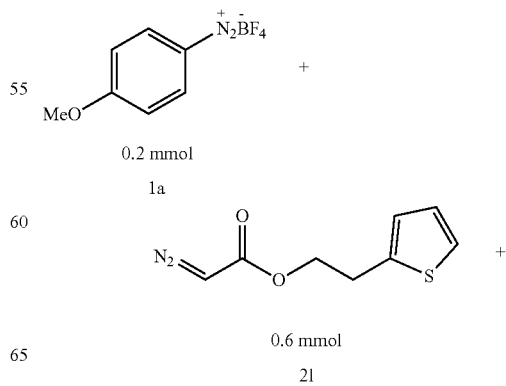

-continued

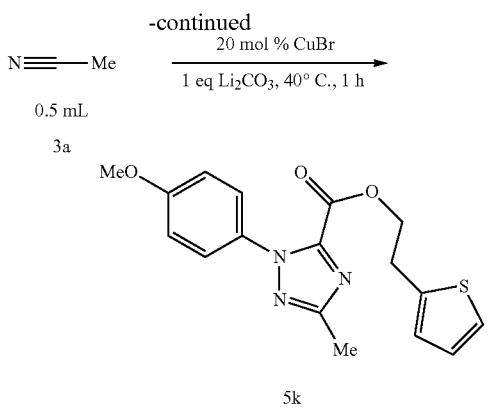

Compound 1a (0.2 mmol, 45.8 mg), CuBr (0.04 mmol, 5.8 mg), Li$_2$CO$_3$ (14.8 mmol), compound 3a (0.5 ml) and compound 2l (0.6 mmol, 120.1 mg) were successively loaded into the reaction flask. Then the system was stirred at 40° C. in air for 1 hour, then quenched with ethyl acetate, the solvent was removed by rotary evaporator, and silica gel adsorption was carried out. The product 5k was obtained by simple column chromatography with a yield of 74%. The main test data of the product are as follows. The analysis shows that the actual synthetic product is consistent with the theoretical analysis.

$^1$H NMR (400 MHz, CDCl$_3$) δ 7.34-7.28 (m, 2H), 7.15 (m, 1H), 6.94 (m, 3H), 6.83 (d, J=3.4 Hz, 1H), 4.51 (t, J=7.2 Hz, 2H), 3.85 (s, 3H), 3.23 (t, J=7.2 Hz, 2H), 2.51 (s, 3H). $^{13}$C NMR (101 MHz, CDCl$_3$) δ 160.83, 160.18, 157.12, 144.43, 138.58, 130.62, 126.92, 126.79, 125.73, 124.12, 113.90, 66.15, 55.45, 28.86, 13.75. HRMS (ESI-TOF): Anal. Calcd. For C$_{17}$H$_{17}$N$_3$O$_3$S+H$^+$: 344.1063, Found: 344.1070; IR (neat, cm$^{-1}$): ν 2924.64, 1738.29, 1517.78, 1252.31, 1222.75, 1115.15, 835.11, 719.94.

Example 29

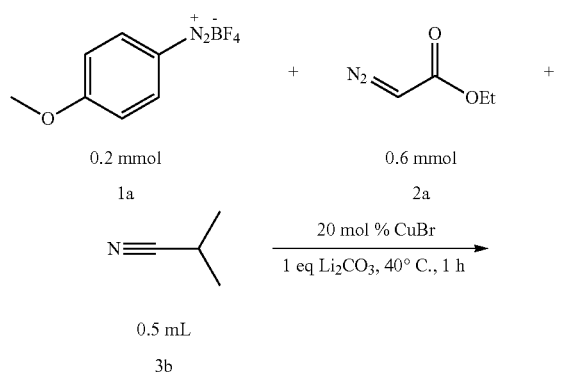

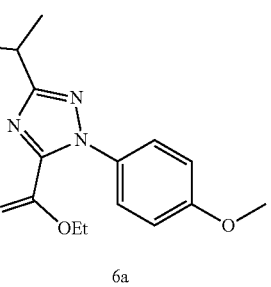

Compound 1a (0.2 mmol, 45.8 mg), CuBr (0.04 mmol, 5.8 mg), Li$_2$CO$_3$ (14.8 mmol), compound 3b (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 6a was obtained by simple column chromatography with a yield of 76%. The main test data of the product are as follows. The analysis shows that the actual synthetic product is consistent with the theoretical analysis.

$^1$H NMR (400 MHz, CDCl$_3$) δ 7.39-7.32 (m, 2H), 7.01-6.94 (m, 2H), 4.36 (q, J=8.0 Hz, 2H), 3.85 (s, 3H), 3.19 (dt, J=13.9, 7.0 Hz, 1H), 1.40 (d, J=8.0 Hz, 6H), 1.32 (t, J=8.0 Hz, 3H). $^{13}$C NMR (101 MHz, CDCl$_3$) δ 169.13, 160.11, 157.52, 144.66, 130.93, 126.93, 113.85, 62.34, 55.44, 28.24, 21.45, 13.92. HRMS (ESI-TOF): Anal. Calcd. For C$_{15}$H$_{19}$N$_3$O$_3$+H$^+$: 290.1499, Found: 290.1502; IR (neat, cm$^{-1}$): ν 2975.31, 1729.47, 1520.10, 1487.75, 1256.44, 1288.07, 1121.29, 830.85.

Example 30

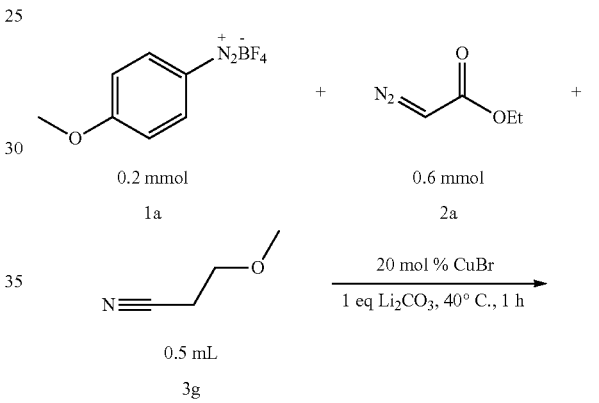

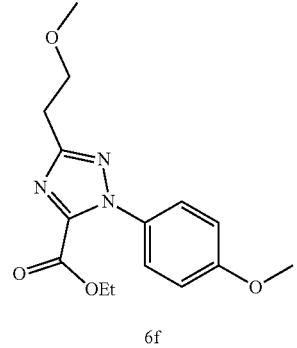

Compound 1a (0.2 mmol, 45.8 mg), CuBr (0.04 mmol, 5.8 mg), Li$_2$CO$_3$ (14.8 mmol), compound 3g (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 6f was obtained by simple column chromatography with a yield of 52%. The main test data of the product are as follows. The analysis shows that the actual synthetic product is consistent with the theoretical analysis.

$^1$H NMR (400 MHz, CDCl$_3$) δ 7.40-7.30 (m, 2H), 7.04-6.89 (m, 2H), 4.36 (q, J=8.0 Hz, 2H), 3.91-3.81 (m, 5H), 3.39 (s, 3H), 3.12 (t, J=7.0 Hz, 2H), 1.33 (t, J=8.0 Hz, 3H). 13C NMR (101 MHz, CDCl$_3$) δ 161.68, 160.23, 157.35, 144.91, 130.77, 126.96, 113.89, 70.35, 62.48, 58.61, 55.51, 28.80, 13.98. HRMS (ESI-TOF): Anal. Calcd. For C$_{15}$H$_{19}$N$_3$O$_4$+H$^+$: 306.1448, Found: 306.1459; IR (neat, cm$^{-1}$): ν 2918.89, 1732.21, 1520.34, 1251.13, 1235.39, 1109.39, 1033.58, 832.50.

Example 31

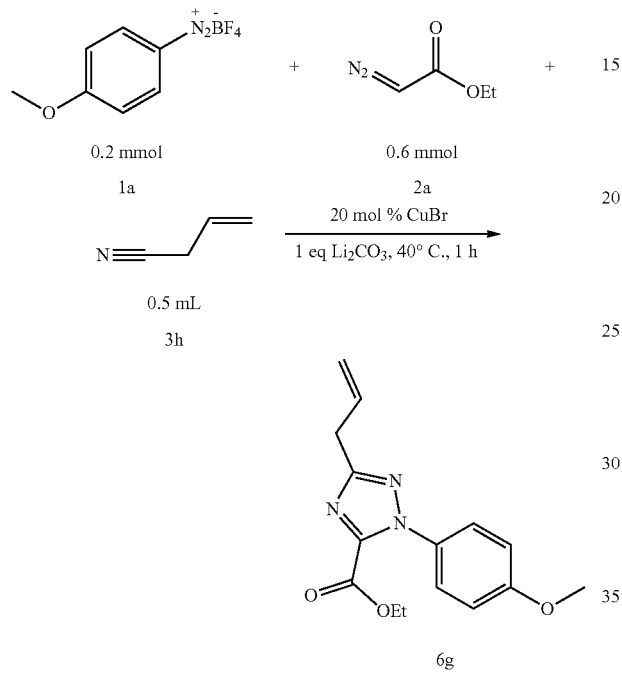

Compound 1a (0.2 mmol, 45.8 mg), CuBr (0.04 mmol, 5.8 mg), Li$_2$CO$_3$ (14.8 mmol), compound 3h (0.5 ml) and compound 2a (0.6 mmol, 72.1 mg) were successively loaded into the reaction flask. Then the system was stirred at 40° C. in air for 1 hour, then quenched with ethyl acetate, the solvent was removed by rotary evaporator, and silica gel adsorption was carried out. The product 6g was obtained by simple column chromatography with a yield of 85%. The main test data of the product are as follows. The analysis shows that the actual synthetic product is consistent with the theoretical analysis.

$^1$H NMR (400 MHz, CDCl$_3$) δ 7.43-7.29 (m, 2H), 7.07-6.89 (m, 2H), 6.11 (m, 1H), 5.37-5.06 (m, 2H), 4.36 (q, J=8.0 Hz, 2H), 3.86 (s, 3H), 3.62 (dt, J=6.7, 1.3 Hz, 2H), 1.33 (t, J=8.0 Hz, 3H). $^{13}$C NMR (101 MHz, CDCl$_3$) δ 162.56, 160.23, 157.32, 144.92, 133.27, 130.72, 126.94, 117.52, 113.89, 62.46, 55.48, 32.84, 13.96. HRMS (ESI-TOF): Anal. Calcd. For C$_{15}$H$_{17}$N$_3$O$_3$+H$^+$: 288.1343, Found: 288.1337; IR (neat, cm$^{-1}$): ν 2928.33, 1731.60, 1250.04, 1305.39, 1259.80, 1223.27, 1110.08, 853.01.

The invention claimed is:

1. A method of preparing a 1,2,4-triazole, comprising: conducting a cyclization reaction of a fluoroborate aryl diazonium salt, a diazonium ester derivative and an organic nitrile, in the presence of a copper salt as a catalyst and an inorganic base as an additive, to obtain the 1,2,4-triazole, wherein the fluoroborate aryl diazonium salt has the following chemical structural formula:

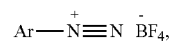

and Ar is selected from the group consisting of an aryl group, a monosubstituted aryl group, a disubstituted aryl group, and naphthyl;

wherein the diazonium ester derivative has the following chemical formula:

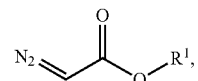

and R$^1$ is selected from the group consisting of ethyl, isopropyl, tert-butyl, cyclohexyl, phenyl, benzyl,

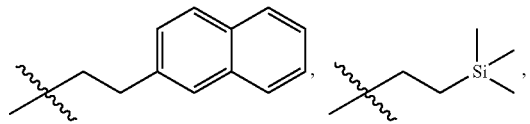

—CH$_2$CH$_2$CH$_2$OCH$_3$, —CH$_2$CF$_3$, —CH$_2$CH$_2$Br,

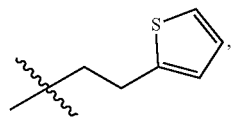 [SMILES: *CCc1cccs1]

and —CH$_2$CH$_2$CH=CH$_2$;

wherein the organic nitrile has the following chemical structural formula: R$^2$—C≡N, and R$^2$ is selected form the group consisting of methyl, isopropyl, tert-butyl, benzyl, —CH$_2$CH$_2$CH$_2$Cl, —CH$_2$CH$_2$OCH$_3$, —CH$_2$CH=CH$_2$, —CH=CHCH$_3$, and

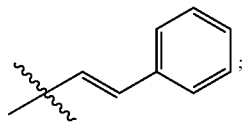 [SMILES: */C=C/c1ccccc1]

wherein the 1,2,4-triazole has the following chemical structural formula:

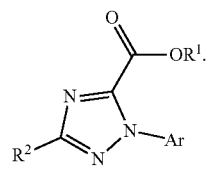

2. The method according to claim 1, wherein the cyclization reaction is conducted at 40° C. for 1 hour in the air.

3. The method according to claim 1, wherein the copper salt was a halogen copper salt, and the additive is selected from the group consisting of lithium carbonate, potassium carbonate, cesium carbonate, sodium acetate, and lithium tert-butoxide.

4. The method according to claim 3, wherein the copper salt is cuprous bromide, and the additive is lithium carbonate.

5. The method according to claim 1, wherein the aryl group is phenyl; the monosubstituted aryl group has the following chemical structural formula:

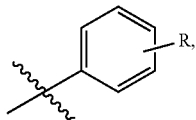

and R is selected from the group consisting of hydrogen, methyl, isopropyl, tert-butyl, isopropyl, methoxy, fluoride, chlorine, bromine, trifluoromethyl, and trifluoromethoxy; and the disubstituted aryl group is selected from the group consisting of

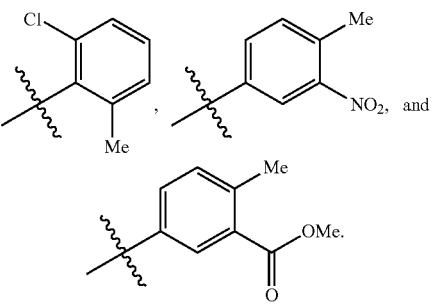

6. The method according to claim 1, wherein a molar ratio of the catalyst to the fluoroborate aryl diazonium salt is 20%; and a molar ratio of the additive to the fluoroborate aryl diazonium salt is 1.

7. The method according to claim 1, wherein a molar ratio of the organic nitrile to the fluoroborate aryl diazonium salt is 20-50; and a molar ratio of the diazonium ester derivative to the fluoroborate aryl diazonium salt is 3.

* * * * *